United States Patent [19]

Harris

[11] Patent Number: 4,631,051
[45] Date of Patent: Dec. 23, 1986

[54] VENTRICULAR AMNIOTIC SHUNT AND INTRODUCER SYSTEM

[75] Inventor: Donald L. Harris, Key Largo, Fla.

[73] Assignee: Cordis Corporation, Miami, Fla.

[21] Appl. No.: 653,340

[22] Filed: Sep. 24, 1984

[51] Int. Cl.$^4$ .................... A61M 27/00; A61M 25/00
[52] U.S. Cl. ...................................... 604/9; 604/164; 604/169
[58] Field of Search ............... 604/8, 9, 10, 128, 129, 604/164, 169, 165

[56] References Cited

U.S. PATENT DOCUMENTS

| | | |
|---|---|---|
| 3,288,142 | 11/1966 | Hakim . |
| 3,527,226 | 9/1970 | Hakim . |
| 3,894,541 | 7/1975 | El-Shafei ............................... 604/10 |
| 4,166,469 | 9/1979 | Littleford ............................. 604/164 |
| 4,215,695 | 8/1980 | Spitz et al. ............................... 604/9 |
| 4,382,445 | 5/1983 | Sommers ................................ 604/8 |
| 4,413,985 | 11/1983 | Wellner et al. ........................ 604/9 |
| 4,416,273 | 11/1983 | Grimes ................................. 604/283 |
| 4,474,569 | 9/1984 | Newkirk ................................ 604/8 |
| 4,475,898 | 10/1984 | Brodner et al. ........................ 604/9 |

OTHER PUBLICATIONS

Article, "In Utero Diagnosis and Treatment of Non-Human Primate Fetal Skeletal Anomalies", Michejda and Hogden, from *Journal of the American Medical Association,* vol. 246, No. 10, pp. 1093-1097, Sep. 4, 1981.

Article, "Fetal Surgery: Saving the Unborn", Freiherr, from *Research Resources Reporter,* vol. VII, No. 2, Feb., 1983.

*Primary Examiner*—Stephen C. Pellegrino
*Assistant Examiner*—Mark Rooney
*Attorney, Agent, or Firm*—Lockwood, Alex, Fitzgibbon & Cummings

[57] ABSTRACT

Cerebrospinal fluid is drained from a ventricle of the brain of a fetus and into the amniotic cavity in an antenatal procedure that does not require a hysterotomy, such being carried out by a shunt and introducer system. The introducer portion of the system includes a plurality of components that are slidably assembled and that provide a guiding sheath through which the shunt is passed with the aid of a pushing tool and a stylet that passes through the pushing tool and into the shunt. The hydrocephalus valve within the shunt is radially offset from the longitudinal axis of the shunt in order to permit stylet passage therethrough.

26 Claims, 8 Drawing Figures

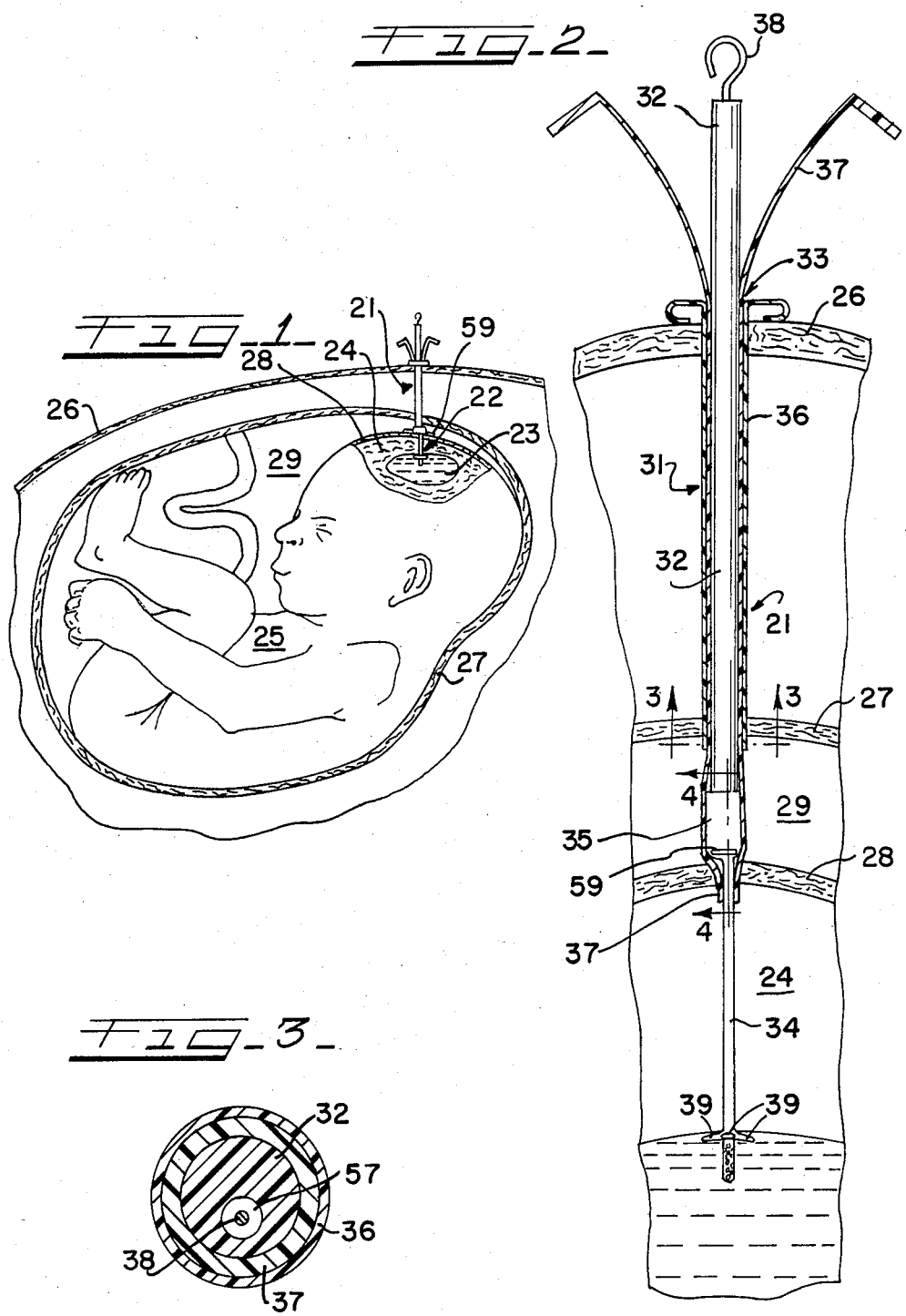

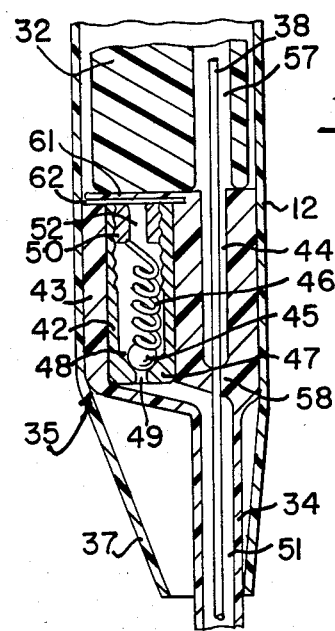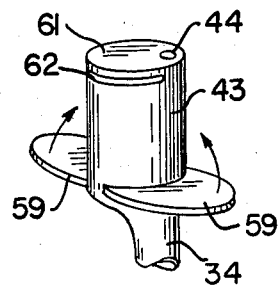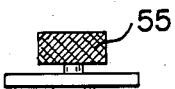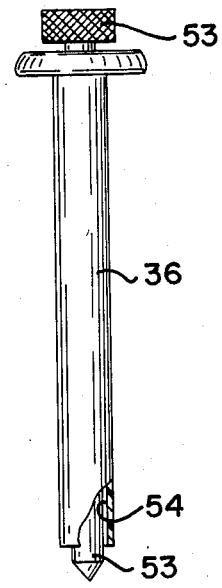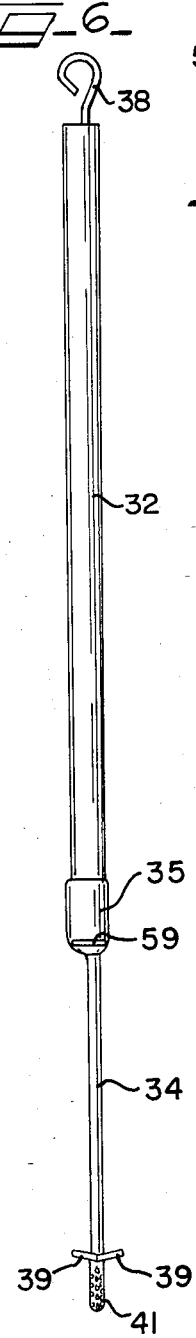

VENTRICULAR AMNIOTIC SHUNT AND INTRODUCER SYSTEM

DESCRIPTION

This invention generally relates to the drainage of cerebrospinal fluid from a ventricle of the brain, particularly the removal of cerebrospinal fluid from a ventricle of the brain of a fetus. The invention includes a plurality of components that are slidably assembled in order to provide an introducer system for a cerebrospinal fluid drainage valve assembly that includes a catheter for providing a fluid passageway between the ventricle and a one-way valve which is positioned external of the fetal skull and within the amniotic cavity, which is internal of the uterine wall.

Hydrocephalus is a condition characterized by an abnormal increase in the amount of cerebrospinal fluid within the brain cavity, which is usually accompanied by an enlargement of the head and which typically leads to brain damage. Hydrocephalus has been treated for a number of years by administering surgical procedures which include implanting a valve or shunt in the skull. Such valves or shunts typically include a catheter having drainage ports that open into a venticle of the brain, the catheter also having a lumen therethrough that allows cerebrospinal fluid to flow from the ports to a one-way valve. These assemblies provide controlled drainage of cerebrospinal fluid out of the ventricle to thereby relieve the build up of cerebrospinal fluid pressure that leads to hydrocephalus or a similar condition. Often, this type of treatment is required for infants. More recently, it has been recognized that hydrocephalus conditions can develop in a fetus and that is can be particularly advantageous to treat hydrocephalus or similar conditions before birth.

Systems have been devised to administer antenatal procedures for intrauterine treatment of hydrocephalus. Michejda and Hodgen, in the article entitled "In Utero Diagnosis and Treatment of Non-Human Primate Fetal Skeletal Anomalies: I. Hydrocephalus", *Journal of the American Medical Association*, Volume 246, No. 10, Page 1093, Sept. 4, 1981, describe a hydrocephalic antenatal vent for intrauterine treatment. This vent is fabricated from stainless steel, and it has external threads for mounting the device within cartilage and bone in a fetal skull through the use of a modified screw-holding screwdriver for facilitating surgical implantation. This vent system also includes a stainless steel ball that is pressed against a tapered seat by a stainless steel spring and a stainless steel set screw for adjusting the pressure applied to the ball. Such a system has the serious disadvantage that implantation is carried out in association with a hysterotomy, which involves incision of the uterus.

A silicone slit valve assembly is described by Freiherr in "Fetal Surgery: Saving the Unborn", *Research Resources Reporter*, Volume VII, No. 2, February, 1983. This slit valve or shunt is implanted in the fetus, typically aided by ultrasonography. The implanted valve is shown as being located within the ventricle of the fetal brain, and a catheter provides a fluid passageway from the ventricle to a location outside of the skull. The one-way slit valve of this system has the disadvantage that its implantation includes passing the valve through the skull and through brain tissue in order to position it within the ventricle.

There is accordingly a need for a venticular amniotic shunt and introducer system for the relief of hydrocephalus and similar conditions, which system is capable of administering an intrauterine treatment in response to an antenatal diagnosis of such a condition, which treatment accomplishes the drainage of cerebrospinal fluid from a fetus. Most advantageously, this system should preclude the need for hysterotomy, and it should be structured to avoid the need to have the one-way valve itself pass through the fetal skull.

Such accomplishments and advantages have been attained by the present invention which includes an introducer assembly for placing the distal end of a catheter into a ventricle of a fetal brain and for securing a hydrocephalus valve in fluid-passing communication with the proximal end of the catheter such that the valve itself remains external of the skull of the fetus during the remaining term of the pregnancy. The assembly according to this invention includes an elongated pushing tool that slides within a guiding sheath arrangement which extends through the abdominal wall of the woman carrying the fetus and through her uterine wall. Preferably, the guiding sheath arrangement includes a component that also extends through the fetal skull. The distal end of the pushing tool contacts the proximal end of the valve and catheter assembly and, aided by a stylet, the catheter is inserted through the fetal skull by manipulation of the stylet and the pushing tool in a generally distal direction until such time as the distal portion of the catheter is positioned within the venticle as desired. Thereupon, the guiding sheath system, the stylet and the pushing tool are removed in order to leave the hydrocephalus valve and catheter assembly implanted so that cerebrospinal fluid will be drained from the fetal brain and into the amniotic cavity when the cerebrospinal fluid pressure within the ventricle exceeds a predetermined magnitude.

It is accordingly a general object of the present invention to provide an improved ventricular amniotic shunt and introducer system.

Another object of this invention is to provide an improved hydrocephalus valve and catheter assembly in combination with an introducer system for implanting the catheter within the brain while the hydrocephalus valve remains outside of the fetal skull.

Another object of the present invention is to provide an improved apparatus and method that permits intrauterine treatment of hydrocephalus or similar conditions without a hysterotomy.

Another object of this invention is to provide an improved ventricular catheter and introducer system that allows for antenatal treatments and that utilizes a guiding stylet for enhancing the ability of the surgeon to properly locate the catheter within the fetus.

Another object of the present invention is to provide an improved apparatus and method which includes the use of a splittable sheath that provides a guiding pathway for a shunt and pushing tool therefor, which splittable sheath passes through the abdominal wall of the woman carrying the fetus, through her uterine wall, and through the fetal skull.

These and other objects of the present invention will be apparent from the following description of this invention, taken in conjunction with the accompanying drawings, wherein:

FIG. 1 is a generally schematic illustration of the implantation of the ventricular amniotic shunt and introducer system according to this invention;

FIG. 2 is an enlarged detail view, partially in section, of the shunt and introducer system at the stage of its insertion that is prior to that illustrated in FIG. 1;

FIG. 3 is a cross-section along the line 3—3 of FIG. 2;

FIG. 4 is a cross-section along the line 4—4 of FIG. 2;

FIG. 5 is an illustration, in perspective, of a preferred valve housing assembly;

FIG. 6 is an elevational view of the preferred combined pushing tool and shunt assembly according to this invention;

FIG. 7 is an elevational view, partially broken away, of the cannula which forms a portion of the preferred guiding assembly according to this invention; and FIG. 8 is an elevational view, partially broken away, of the splittable sheath that is included within the preferred guiding assembly according to this invention.

A ventricular amniotic shunt and introducer system, generally designated as 21, is illustrated in FIGS. 1 and 2 at a position after the shunt, generally shown at 22, has been inserted into a ventricle 23 in the brain 24 of a fetus 25. The amniotic shunt and introducer system 21 is shown passing through the abdominal wall 26 of the woman carrying the fetus and through her uterine wall 27. Portions of the system 21 also pass through the fetal skull 28 of the fetus 25 while same is suspended within the amniotic cavity 29.

With more particular reference to the ventricular amniotic shunt and introducer system 21, same generally includes an introducer assembly, generally designated as 31, which includes a pushing tool 32 and a guiding sheath assembly, generally designated as 33. The ventricular amniotic shunt and introducer system 21 also includes the shunt 22, which includes a catheter 34 and a valve assembly 35 at the proximal portion thereof. In the preferred embodiment, the guiding sheath assembly 33 includes a cannula 36 and a splittable sheath 37 that is inserted within the cannula 36. The introducer assembly 31 further includes a stylet 38. Catheter 34 includes a flange assembly, which preferably includes four flanges 39, and at least one orifice 41 that is located distally of the flanges 39.

Valve assembly 35, which is shown more particularly in FIGS. 4 and 5, includes a hydrocephalus or one-way valve 42 mounted within a housing 43. In an important aspect of this invention, the housing 43 includes a partial lumen 44, and the valve 42 is offset with respect to the partial lumen 44 so that the stylet 38 can pass through the valve assembly 35 without interference from or damage to the one-way valve 42. Housing 43 may advantageously be provided with a hinged cap or flap 61 which is separated from the rest of the housing 43 by a slit 62. Flap 61 reduces the chance that debris in the amniotic fluid will enter the valve opening 52 while still allowing for passage of cerebrospinal fluid out of the valve assembly 35.

One-way valve 42 is a valve that is suitable for treatment of fetal or pediatric hydrocephalus. Found to be especially advantageous are spring-biased valves such as those illustrated in FIG. 4. Valves of this type include a ball or sphere 45, typically a synthetic sapphire, and a generally spiral spring 46, typically stainless steel, both of which are mounted within a valve body 47, preferably also stainless steel. Valve body 47 includes a generally conically shaped bore 48 of a passageway 49 through the valve body 47 and thus through the one-way valve 42 and the valve assembly 35. One end of the spring 46 engages and supports the sphere 45, while the other end of the spring 46 is secured to a threaded plug 50.

The resistance provided by the valve spring 46 determines the cerebrospinal fluid pressure at which the cerebrospinal fluid within the ventricle 23 and lumen 51 of the catheter 34 will move the sphere 45 from its seated position within the conically-shaped bore 48 in order to thereby control the flow of cerebrospinal fluid through the lumen 51, the passageway 49 and its bore 48, and out of the valve assembly 35 through an opening 52 through the threaded plug 50. When implanted, the opening 52 opens into the amniotic cavity 29, whereby the cerebrospinal fluid passing through the valve assembly 35 enters the amniotic fluid. Tension in the spring 46, and thus the resistance to fluid flow that is provided by the valve assembly 35, is adjusted by rotating the threaded plug 50 to threadedly move same and one end of the spring 46 closer to or farther away from the sphere 45. Such rotation may be provided, for example, by inserting a wrench into the opening 52, which may be hexagonal.

With more particular reference to the preferred introducer assembly 31, such includes the splittable sheath 37 inserted into the cannula 36, with the pushing tool 32 being within the splittable sheath 37. Preferably, each of these components is inserted separately during the implantation procedure that is aided by ultrasonography. More particularly, the cannula 36 (see FIG. 7) is preferably first inserted, with the aid of its needle 53, through the abdominal wall 26 and the uterine wall 27, after which the needle 53 is withdrawn from the lumen 54 of the cannula 36. At this point, the lumen 54 of the inserted cannula provides a slidable passageway from a location external of the abdominal wall 26 to a location internal of the uterine wall 27. Preferably, the cannula 36 has an outer diameter of about 8 mm, is about 8 cm long, and is made of a material having a relatively low coefficient of friction, such as polytetrafluoroethylene (Teflon), polypropylene, or the like.

Splittable sheath 37 (see FIG. 8), which is preferably fabricated of a generally tearable polyolefin material such as a polyethylene, is approximately 3.5 mm in diameter (French 10-½) and from about 10 to 10.5 cm in length. Splittable sheath 37 is inserted, with the aid of its needle 55, into the lumen 54 of the inserted cannula 36. Such insertion proceeds until the needle 55 and the splittable sheath 37 pass distally (or internally) of the uterine wall 27 and the distal end of the cannula 36. Insertion continues until such time as the needle 55 punctures the fetal skull 28 at a predetermined location selected by the surgeon so that the distal end of the splittable sheath 37 is positioned through the fetal skull 28 and into the brain 24, and in general alignment with the venticle 23. Thereafter, the needle 55 is removed from lumen 56 of the splittable sheath 37.

Splittable sheath 37 is designed to provide a sever line in the sleeve wall or to be weak enough to aid severing along at least a substantial length of the sheath 37, such as is generally described in U.S. Ltrs. Pat. No. 4,166,469, the subject matter thereof being incorporated by reference hereinto. By such design, the splittable sheath 37 will split longitudinally, which is typically initiated by pulling the sheath 37 apart, when a component such as the valve assembly 35 and the pushing tool 32 pass therethrough in order to thereby effectively guide the catheter 34 through the brain 24 and into the venticle 23 while permitting passage of the valve assembly 35 and the pushing tool 32, which are larger in cross-section than is the catheter 34. Typically, the valve housing 43 has an outer diameter of about 7 mm, and the valve assembly 35 has a length of about 6.5 mm.

Referring more particularly to the combination of the pushing tool 32 and the valve assembly 35, FIG. 6 illustrates the relationship therebetween during the implantation procedure. The distal end of the pushing tool 32 is butted against the proximal end of the valve assembly 35. As illustrated in FIG. 4, the stylet 38 located within lumen 57 of the pushing tool 32 is inserted into the partial lumen 44 of the valve assembly 35 until such time as section 58 of the housing 43 is pierced by the stylet 38 in order to permit passage of the stylet 38 through the lumen 51 of the catheter 34. The distal end of the stylet 38 proceeds to the distal end of the catheter 34 and guides the catheter 34 through brain tissue and to the ventricle 23.

Insertion is continued until such time as the flanges 39 of the catheter 34 enter the ventricle 23 through force applied by the hands of the surgeon which is adequate to fold back the flanges 39. Such flanges 39 function, in cooperation with the distal surface of the valve housing 43 and ears 59, to maintain this position of the shunt 22 after the introducer assembly 31 and its stylet 38 have been removed through the abdominal wall 26. Removal includes pulling the splittable sheath 37 out of the patient while firmly holding the pushing tool 32. Next, the stylet 38 is removed while the pushing tool 32 is firmly held in place. Finally, the cannula 36 and the pushing tool 32 are removed from the patient to complete the implantation procedure.

Upon such removal of the stylet 38, the pierced section 58 of the valve housing 43 closes to a degree adequate to prevent cerebrospinal fluid leakage therethrough after implanation has been completed. Such closing may be assisted by passing a needle through section 58 during manufacturing of the shunt 22. Puncturing the section 58 with this needle, which has a diameter less than that of the stylet 38, forms a guiding pathway for the stylet 38 which closes more effectively than a larger diameter hole that would be made by having the stylet 38 itself puncture section 58.

Once thus positioned, implantation is complete, and the valve assembly 35 functions to drain cerebrospinal fluid from the ventricle and into the amniotic cavity 29 whenever the cerebrospinal fluid pressure within the ventricle 23 exceeds a predetermined magnitude. The cerebrospinal fluid flows through the orifice 41, the lumen 51, the valve assembly 35, the opening 52, and the slit 62.

Typical fetal hydrocephalus pressures can be as high as 100 mm of water, which pressure is relieved by this invention. Amniotic fluid is prevented from flowing through the one-way valve 42 and thus into the ventricle 23 because the pressure of the amniotic fluid, which typically will be between 0 and 20 mm of water, forces the one-way valve 42 to close when the cerebrospinal fluid pressure is lower than the amniotic fluid pressure. Additionally, because the one-way valve 42 and its somewhat large housing 43 are positioned external of the fetal skull 28, amniotic fluid pressure cannot force the valve assembly 35 into the fetal brain 28. This feature is enhanced by providing the flanges or ears 59 that collapse upwardly in the direction of the arrows shown in FIG. 5 when the catheter 34 and valve housing 43 are fed through the guiding assembly 33 and that engage the outer surface of the fetal skull 28 when the guiding assembly 33 is removed.

It is to be appreciated that this invention can be embodied in various forms and therefore is to be construed and limited only by the scope of the appended claims.

I claim:

1. A ventricular amniotic shunt and introducer system for the relief of fetal hydrocephalus, comprising:
   an introducer assembly including a guiding assembly having a longitudinal lumen therethrough;
   a pushing tool of said introducer assembly, said pushing tool including an elongated rod insertable through said longitudinal lumen of the introducer assembly, said pushing tool having a distal end, and said pushing tool including a stylet slidable through a lumen of said pushing tool elongated rod;
   a valve assembly inserted through said longitudinal lumen of the introducer assembly and inclining a hydrocephalus valve mounted within a valve housing and a catheter depending from said valve housing, said valve having an inflow end and an outflow end, said catheter having a distal end, said catheter and said valve inflow end housing having a common passageway between the hydrocephalus valve and the distal end of the catheter, said valve assembly having a top end, and said valve housing includes a stylet guiding partial lumen longitudinally positioned therewith and spaced from said common passageway;
   the distal end of the pushing tool pushingly engages the top end of the valve assembly; and
   an orifice is included at the distal end of the catheter, and an opening in said top end of the valve assembly is in fluid-passing communication with the outflow end of the hydrocephalus valve, said orifice being in fluid-passing communication with the inflow end of the hydrocephalus valve through said common passageway.

2. The system according to claim 1, wherein said introducer assembly includes a plurality of slidably insertable components.

3. The system according to claim 1, wherein said hydrocephalus valve is a one-way valve that permits fluid flow between said inflow end and said outflow end in response to pressure having a predetermined magnitude.

4. The system according to claim 1, wherein said valve assembly, when implanted in a fetal skull, has its valve housing external of the fetal skull.

5. The system according to claim 1, wherein said guiding sheath assembly includes a cannula and a splittable sheath slidably mountable through said cannula.

6. The system according to claim 1, wherein said catheter of the valve assembly includes an external flange and an ear, both said flange and said ear being located proximally of said catheter orifice and substantially distally of said valve housing, said flange and said ear being spaced apart through a length approximately equal to the distance between the fetal skull and fetal ventricle from which cerebrospinal fluid is to be drained.

7. A ventricular amniotic shunt and introducer system for the relief of fetal hydrocephalus, comprising:
   an introducer assembly including a guiding assembly having a longitudinal lumen therethrough;
   a pushing tool of said introducer assembly, said pushing tool being an elongated rod insertable through said longitudinal lumen of the introducer assembly, said pushing tool having a distal end;

a valve assembly inserted through said longitudinal lumen of the introducer assembly and including a hydrocephalus valve mounted within a valve housing and a catheter depending from said valve housing, said valve having an inflow end and an outflow end, said catheter having a distal end, said catheter and said valve housing having a common passageway providing fluid flow communication between the hydrocephalus valve and the distal end of the catheter, said valve assembly having a top end, and said valve housing includes a stylet guiding partial lumen longitudinally positioned therewithin and separated from said fluid flow common passageway through a section of the valve assembly, and wherein said hydrocephalus valve is radially offset with respect to the axis of said partial lumen;

the distal end of the pushing tool pushingly engages the top end of the valve assembly; and an orifice is included at the distal end of the catheter, and an opening in said top end of the valve assembly is in fluid-passing communication with the outflow end of the hydrocephalus valve, said orifice being in fluid-passing communication with the inflow end of the hydrocephalus valve through said common passageway.

8. The system according to claim 1, wherein said valve housing includes a hinged cap over the outflow end of the hydrocephalus valve.

9. The system according to claim 1, wherein said hydrocephalus valve includes a valve body having a conically shaped bore located between said inflow end and said ouflow end, a sphere mounted within said conically shaped bore, and a spring that seats said sphere in said conically shaped bore.

10. A ventricular amniotic shunt and introducer system for the relief of fetal hydrocephalus, comprising:

an introducer assembly including a cannula and a splittable sheath inserted completely through the entire length of said cannula, said splittable sheath having a lumen therethrough;

a pushing tool of said introducer assembly, said pushing tool including an elongated rod insertable through said lumen of the splittable sheath, said pushing tool having a distal end, and said pushing tool including a stylet slidable through a lumen of said pushing tool elongated rod;

a valve assembly including a hydrocephalus valve mounted within a valve housing and a catheter depending from said valve housing, said hydrocephalus valve having an inflow end and an outflow end, said catheter having a distal end, said catheter and said valve housing having a common passageway that is uninterrupted between the hydrocephalus valve inflow end and the distal end of the catheter, said valve assembly having a top end and said valve housing includes a stylet guiding partial lumen longitudinally positioned therewith and spaced from said common passageway;

the distal end of the pushing tool butts against the top end of the valve assembly; and an orifice is included at the distal end of the catheter, and an opening in said top end of the valve assembly is in fluid passing communication with the outflow end of the hydrocephalus valve, said orifice being in fluid-passing communication with the inflow end of the hydrocephalus valve through said common passageway.

11. The fetal hydrocephalus relief system according to claim 10, further including a flange positioned along the length of the catheter substantially immediately proximally spaced from said orifice.

12. A ventricular amniotic shunt and introducer system for the relief of fetal hydrocephalus, comprising:

an introducer assembly including a cannula and a splittable sheath inserted completely through the entire length of said cannula, said splittable sheath having a lumen therethrough;

a pushing tool of said introducer assembly, said pushing tool being an elongated rod insertable through said lumen of the splittable sheath, said pushing tool having a distal end;

a valve assembly including a hydrocephalus valve mounted within a valve housing and a catheter depending from said valve housing, said hydrocephalus valve having an inflow end and an outflow end, said catheter having a distal end, said catheter and said valve housing having a common passageway that is uninterrupted and that provides fluid flow communication between the hydrocephalus valve and the distal end of the catheter, said valve assembly having a top end, and said valve housing includes a stylet guiding partial lumen longitudinally positioned therewithin and separated from said fluid flow common passageway through a section of the valve assembly, and wherein said hydrocephalus valve is radially offset with respect to the axis of said partial lumen;

the distal end of the pushing tool butts against the top end of the valve assembly; and an orifice is included at the distal end of the catheter, and an opening in said top end of the valve assembly is in fluid passing communication with the outflow end of the hydrocephalus valve, said orifice being in fluid-passing communication with the inflow end of the hydrocephalus valve through said common passageway.

13. The fetal hydrocephalus relief system according to claim 10, wherein said valve housing includes a hinged cap over the outflow end of the hydrocephalus valve.

14. A method for treating fetal hydrocephalus comprising:

passing a needle through a lumen of a cannula, inserting the needle and cannula through a woman's abdominal wall and uterine wall, and removing the needle from the cannula while leaving the cannula inserted through the abdominal wall and uterine wall;

passing a needle through a lumen of an elongated sheath, inserting the needle and elongated sheath through the lumen of the cannula that is inserted through the abdominal wall and uterine wall, continuing with said elongated sheath inserting step until said needle and elongated sheath pass through the skull of a fetus within the uterine wall, and removing this needle from the thus inserted elongated sheath;

pushingly engaging a top end of a hydrocephalus valve assembly with the distal end of a pushing tool and manipulating the pushing tool to feed the hydrocephalus valve assembly through the lumen of the inserted elongated sheath until an orifice of the hydrocephalus valve assembly enters a ventricle of the brain of the fetus, said hydrocephalus valve assembly including a hydrocephalus valve and a fluid flow passageway between said valve and said orifice;

slidably removing the elongated sheath, the pushing tool and the cannula while leaving the hydrocephalus valve assembly implanted within the fetal skull; and said step of manipulating the pushing tool to feed the hydrocephalus valve assembly through the inserted elongated sheath includes inserting a stylet longitudinally through a lumen of the pushing tool and then through a stylet guiding partial lumen of the hydrocephalus valve assembly to a location at least as distal as the orifice, and wherein said removing step includes slidably removing the stylet.

15. The fetal hydrocephalus treating method according claim 14, wherein said step of manipulating the pushing tool to feed the hydrocephalus valve assembly through the inserted elongated sheath includes longitudinally splitting the inserted elongated sheath.

16. The fetal hydrocephalus treating method according to claim 14, further including permitting cerebrospinal fluid to flow from the ventricle, through the orifice and the hydrocephalus valve assembly, and into the amniotic cavity that is between the fetal skull and the uterine wall.

17. The fetal hydrocephalus treating method according to claim 14, wherein said step of inserting a stylet through the lumen of the hydrocephalus valve assembly includes avoiding the hydrocephalus valve by positioning same at a location radially offset from the lumen of the hydrocephalus valve assembly.

18. The fetal hydrocephalus treating method according to claim 14, wherein said stylet inserting step includes piercing a section of the hydrocephalus valve assembly with the stylet, said section being adjacent said stylet guiding partial lumen of the hydrocephalus valve assembly.

19. The system according to claim 7, wherein said hydrocephalus valve is a one-way valve that permits fluid flow between said inflow end and said outflow end in response to pressure having a predetermined magnitude.

20. The system according to claim 7, wherein said valve assembly, when implanted in a fetal skull, has its valve housing external of the fetal skull.

21. The system according to claim 7, wherein said guiding assembly includes a cannula and a splittable sheath slidably mountable through said cannula.

22. The system according to claim 7, wherein said catheter of the valve assembly includes an external flange and an ear, both said flange and said ear being located proximally of said catheter orifice and substantially distally of said valve housing, said flange and said ear being spaced apart through a length approximately equal to the distance between the fetal skull and fetal ventricle from which cerebrospinal fluid is to be drained.

23. The system according to claim 7, wherein said valve housing includes a hinged cap over the outflow end of the hydrocephalus valve.

24. The system according to claim 7, wherein said hydrocephalus valve includes a valve body having a conically shaped bore located between said inflow end and said outflow end, a sphere mounted within said conically shaped bore, and a spring that seats said sphere in said conically shaped bore.

25. The fetal hydrocephalus relief system according to claim 12, further including a flange positioned along the length of the catheter substantially immediately proximally spaced from said orifice.

26. The fetal hydrocephalus relief system according to claim 12, wherein said valve housing includes a hinged cap over the outflow end of the hydrocephalus valve.

* * * * *

UNITED STATES PATENT AND TRADEMARK OFFICE
CERTIFICATE OF CORRECTION

PATENT NO. : 4,631,051
DATED : December 23, 1986
INVENTOR(S) : Donald L. Harris

It is certified that error appears in the above—identified patent and that said Letters Patent is hereby corrected as shown below:

Col. 1, line 26, "venticle" should read --ventricle--; line 35, "is" should read --it--.
    Col. 2, line 30, "venticle" should read --ventricle--.
    Col. 4, line 68, "venticle" should read --ventricle--.
    Col. 5, line 36, "implanation" should read --implantation--.
    Col. 6, line 18, "inclining" should read --including--; line 23, delete "inflow end"; line 24, insert --inflow end-- after "valve".
    Col. 7, line 34, "ouflow" should read --outflow--.

Signed and Sealed this

Twenty-second Day of September, 1987

Attest:

DONALD J. QUIGG

Attesting Officer      Commissioner of Patents and Trademarks